(12) United States Patent
Sasaki et al.

(10) Patent No.: US 11,740,253 B2
(45) Date of Patent: Aug. 29, 2023

(54) AUTOMATIC ANALYZER, AUTOMATIC ANALYSIS SYSTEM, AND DISPLAY METHOD OF REAGENT LIST

(71) Applicant: HITACHI HIGH-TECHNOLOGIES CORPORATION, Tokyo (JP)

(72) Inventors: Hirofumi Sasaki, Tokyo (JP); Toshihide Hanawa, Tokyo (JP); Satoshi Shibuya, Tokyo (JP); Yasuo Kaneko, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 358 days.

(21) Appl. No.: 16/332,055

(22) PCT Filed: Aug. 4, 2017

(86) PCT No.: PCT/JP2017/028357
§ 371 (c)(1),
(2) Date: Mar. 11, 2019

(87) PCT Pub. No.: WO2018/051672
PCT Pub. Date: Mar. 22, 2018

(65) Prior Publication Data
US 2019/0227090 A1    Jul. 25, 2019

(30) Foreign Application Priority Data

Sep. 16, 2016  (JP) .................................. 2016-181134

(51) Int. Cl.
*G01N 35/04*  (2006.01)
*G01N 35/00*  (2006.01)
(Continued)

(52) U.S. Cl.
CPC .............. *G01N 35/04* (2013.01); *G01N 35/00* (2013.01); *G01N 35/00722* (2013.01);
(Continued)

(58) Field of Classification Search
CPC .. G01N 35/04; G01N 35/00; G01N 35/00722; G01N 35/1002; G01N 33/48;
(Continued)

(56) References Cited

U.S. PATENT DOCUMENTS 5,719,059 A    2/1998 Mimura et al.
10,091,279 B2 * 10/2018 Stadnisky ............... H04W 4/80
(Continued)

FOREIGN PATENT DOCUMENTS

CN    1153305 A    7/1997
CN    101126762 A    2/2008
(Continued)

OTHER PUBLICATIONS

International Search Report PCT/JP2017/028357 dated Oct. 24, 2017.
(Continued)

*Primary Examiner* — P. Kathryn Wright
*Assistant Examiner* — Curtis A Thompson
(74) *Attorney, Agent, or Firm* — MATTINGLY & MALUR, PC

(57) ABSTRACT

Provided is an automatic analyzer that can perform a reagent preparation/disposal operation comfortably and smoothly as when printing a reagent list such as a reagent preparation/disposal list on paper even without printing the reagent list. The automatic analyzer that performs analysis using a sample and a reagent, the automatic analyzer including: a storage unit that stores reagent information related to a reagent remaining amount or a reagent expiration date of each of reagent containers; and a display unit that displays a reagent list in which reminder information that gives a reminder to an operator is assigned to each of setting positions of the reagent containers based on the reagent information stored in the storage unit. The reagent managing (Continued)

unit updates display of the reagent list such that a reagent container selected by the operator is visually identifiable while the reagent list is displayed.

4 Claims, 12 Drawing Sheets

(51) Int. Cl.
| | |
|---|---|
| *G01N 35/10* | (2006.01) |
| *B01J 19/00* | (2006.01) |
| *G01N 33/50* | (2006.01) |
| *G01N 33/48* | (2006.01) |
| *G01N 35/02* | (2006.01) |

(52) U.S. Cl.
CPC ............ *G01N 35/1002* (2013.01); *B01J 19/00* (2013.01); *G01N 33/48* (2013.01); *G01N 33/50* (2013.01); *G01N 35/00663* (2013.01); *G01N 35/02* (2013.01); *G01N 35/10* (2013.01); *G01N 2035/0091* (2013.01); *G01N 2035/00673* (2013.01); *G01N 2035/00752* (2013.01); *G01N 2035/0413* (2013.01); *G01N 2035/0443* (2013.01); *G01N 2035/0453* (2013.01)

(58) Field of Classification Search
CPC ........ G01N 35/02; G01N 33/50; G01N 35/10; G01N 35/00663; G01N 2035/00673; G01N 2035/00752; G01N 2035/0091; G01N 2035/0413; G01N 2035/0443; G01N 2035/0453; G01N 2035/009; B01J 19/00
See application file for complete search history.

(56) References Cited

U.S. PATENT DOCUMENTS

| | | | | |
|---|---|---|---|---|
| 2002/0061739 | A1* | 5/2002 | Nakamura | G06F 3/038 455/343.1 |
| 2003/0073069 | A1* | 4/2003 | Selick | G16C 20/30 703/11 |
| 2005/0013736 | A1* | 1/2005 | McKeever | G01N 35/0092 422/63 |
| 2005/0123445 | A1* | 6/2005 | Blecka | G01N 35/025 422/64 |
| 2007/0212261 | A1* | 9/2007 | Tanaka | G01N 35/00663 422/67 |
| 2007/0255756 | A1* | 11/2007 | Satomura | G01N 1/28 |
| 2008/0056939 | A1* | 3/2008 | Awata | G01N 35/00663 422/50 |
| 2008/0063570 | A1* | 3/2008 | Fujino | G01N 35/025 422/400 |
| 2008/0240989 | A1 | 10/2008 | Iwamatsu et al. | |
| 2008/0240991 | A1 | 10/2008 | Wakamiya et al. | |
| 2010/0093097 | A1 | 4/2010 | Kawamura | |
| 2011/0246215 | A1 | 10/2011 | Postma et al. | |
| 2012/0128534 | A1* | 5/2012 | Minemura | G01N 35/00732 422/67 |
| 2012/0275956 | A1 | 11/2012 | Wakamiya et al. | |
| 2013/0224851 | A1* | 8/2013 | Ljungmann | G01N 1/31 435/288.7 |
| 2013/0244274 | A1* | 9/2013 | Nishikawa | G01N 35/00663 435/39 |
| 2013/0260413 | A1* | 10/2013 | Koshimura | G16B 50/00 422/68.1 |
| 2014/0252079 | A1* | 9/2014 | Bjerke | G01N 35/00584 235/375 |
| 2014/0322080 | A1* | 10/2014 | Sarwar | G01N 35/00663 422/67 |
| 2015/0219680 | A1* | 8/2015 | Mimura | G01N 35/1016 436/43 |
| 2020/0049724 | A1* | 2/2020 | Shibuya | G06F 3/0482 |
| 2020/0141960 | A1* | 5/2020 | Tokiwa | G01N 35/04 |

FOREIGN PATENT DOCUMENTS

| | | |
|---|---|---|
| CN | 101275966 A | 10/2008 |
| CN | 103998939 A | 8/2014 |
| EP | 2 796 882 A1 | 10/2014 |
| JP | 10-010134 A | 1/1998 |
| JP | 2009-162584 A | 7/2009 |
| JP | 2010-151672 A | 7/2010 |
| JP | 2012-063237 A | 3/2012 |
| JP | 2012-237734 A | 12/2012 |
| JP | 2013-195130 A | 9/2013 |
| JP | 2015-087225 A | 5/2015 |
| JP | 2015-087843 A | 5/2015 |
| JP | 2015-163896 A | 9/2015 |

OTHER PUBLICATIONS

Extended European Search Report received in corresponding European Application No. 17850578.0 dated May 26, 2020.
Chinese Office Action received in corresponding Chinese Application No. 201780054474.6 dated Dec. 30, 2021.

* cited by examiner

[FIG. 1]
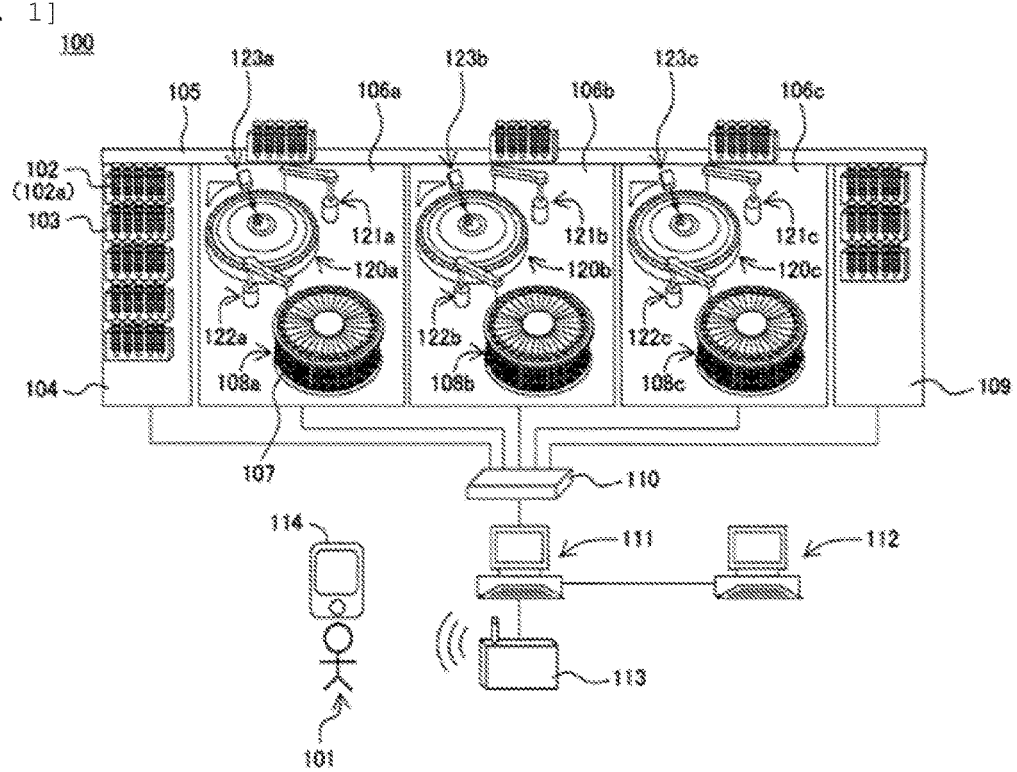
[FIG. 2]
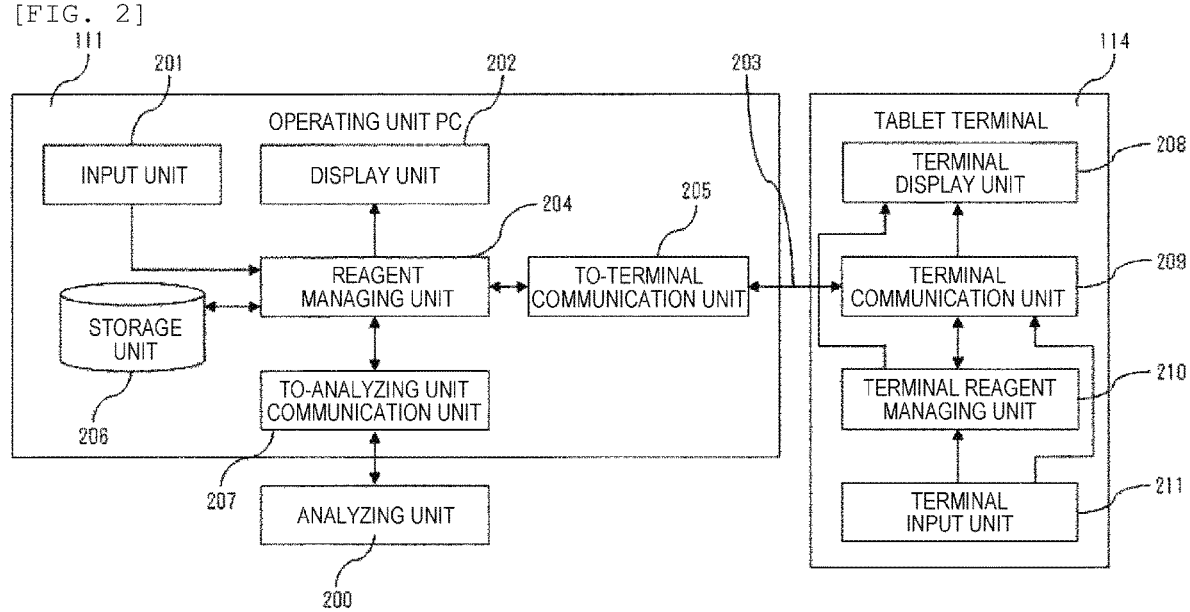

[FIG. 3]

REAGENT PREPARATION LIST

↻ UPDATE DATE: 4/27 11:21

| MODULE | ITEM NAME | POSITION | REMAINING TEST /REMAINING AMOUNT | LEVEL | |
|---|---|---|---|---|---|
| M1 | AST | A-4 | 79 | ATTENTION | ✓ |
| M2 | AST | A-3 | 0 | WARNING | ✓ |
| M1 | LDH | B-16 | 138 | PREPARATION | |
| M2 | LDH | B-17 | 0 | WARNING | ✓ |
| M2 | TP | A-23 | 51 | ATTENTION | ✓ |
| M1 | UA | B-30 | 0 | WARNING | ✓ |
| M1 | DI | A-34 | 49mL | PREPARATION | |
| M2 | DI | B-33 | 0mL | WARNING | ✓ |
| M1 | Hiter | B-35 | 24mL | ATTENTION | ✓ |
| M2 | Cell | - | 350mL | PREPARATION | |

[FIG. 4]

REAGENT PREPARATION LIST

↻ UPDATE DATE: 4/27 11:21

| MODULE | ITEM NAME | POSITION | REMAINING TEST /REMAINING AMOUNT | LEVEL | |
|---|---|---|---|---|---|
| M1 | AST | A-4 | 79 | ATTENTION | OK |
| M2 | AST | A-3 | 0 | WARNING | OK |
| M1 | LDH | B-16 | 138 | PREPARATION | |
| M2 | LDH | B-17 | 0 | WARNING | OK |
| M2 | TP | A-23 | 51 | ATTENTION | OK |
| M1 | UA | B-30 | 0 | WARNING | OK |
| M1 | D1 | A-34 | 49mL | PREPARATION | |
| M2 | D1 | B-33 | 0mL | WARNING | OK |
| M1 | Hiter | B-35 | 24mL | ATTENTION | OK |
| M2 | Cell | - | 350mL | PREPARATION | |

[FIG. 5]

| MODULE | ITEM NAME | POSITION | REMAINING TEST /REMAINING AMOUNT | FACTOR | |
|--------|-----------|----------|----------------------------------|--------|---|
| M2 | AST | A-3 | 0 | REMAINING AMOUNT 0 | ✓ |
| M2 | LDH | B-17 | 0 | REMAINING AMOUNT 0 | ✓ |
| M1 | Mg | A-24 | 179 | EXPIRED | |
| M1 | UA | B-30 | 0 | REMAINING AMOUNT 0 | ✓ |
| M2 | D1 | B-33 | 0mL | REMAINING AMOUNT 0 | ✓ |

REAGENT DISPOSAL LIST

UPDATE DATE: 4/27 11:21

[FIG. 6]
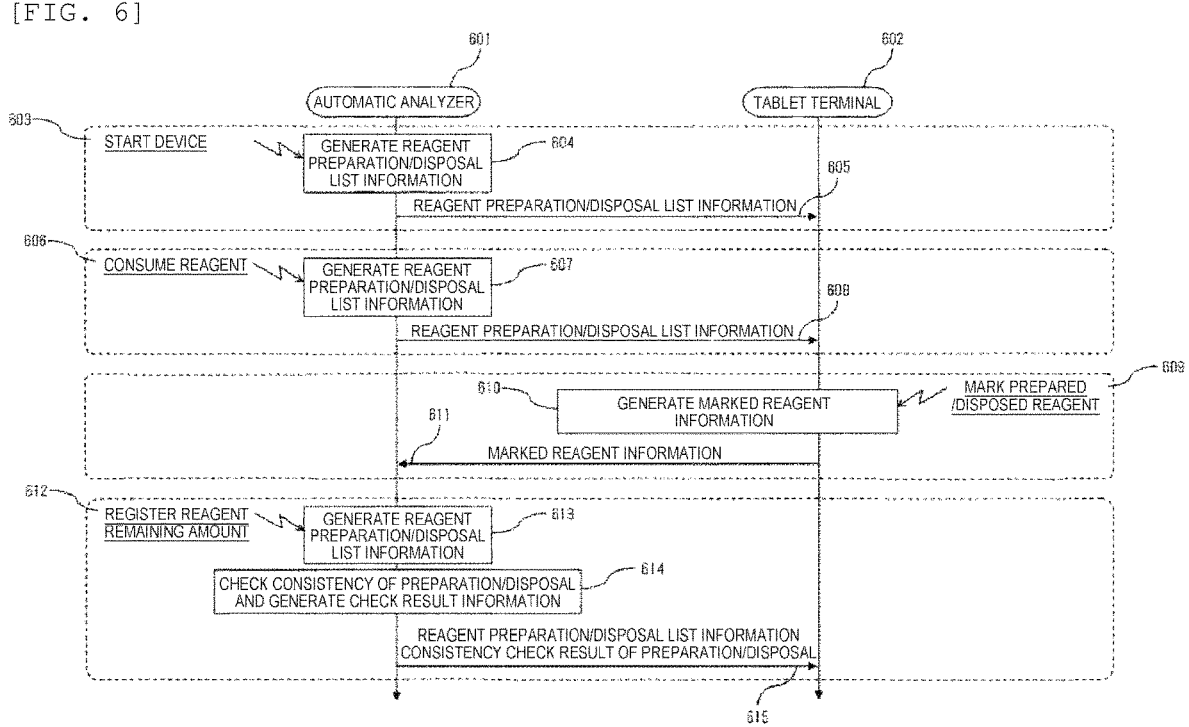

[FIG. 7]
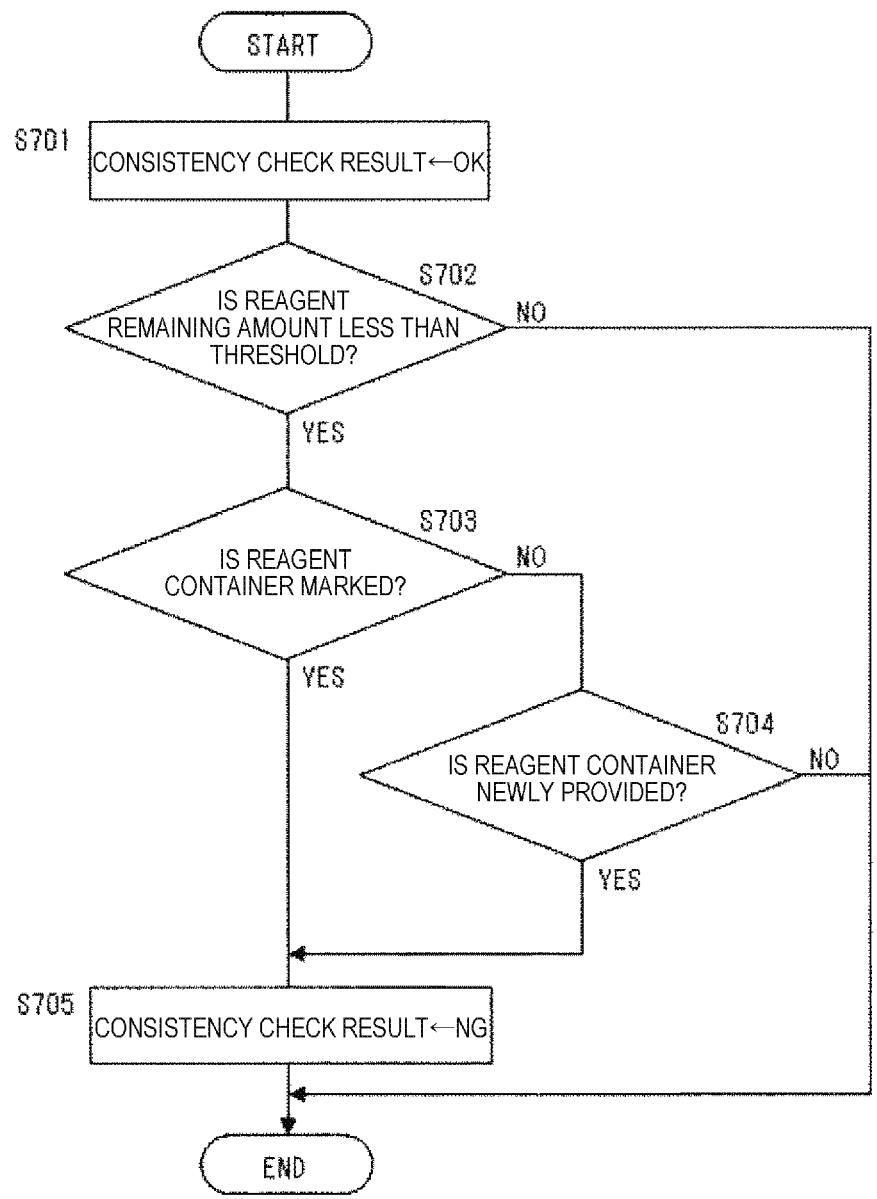

[FIG. 8]
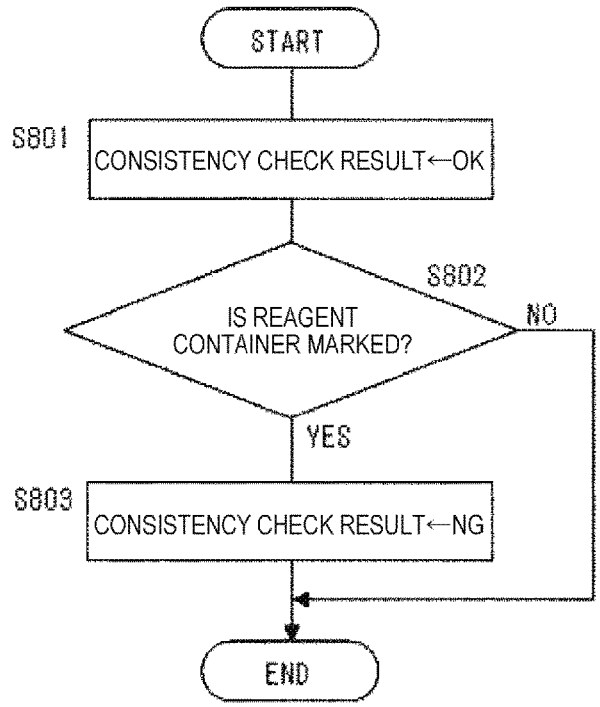
[FIG. 9]
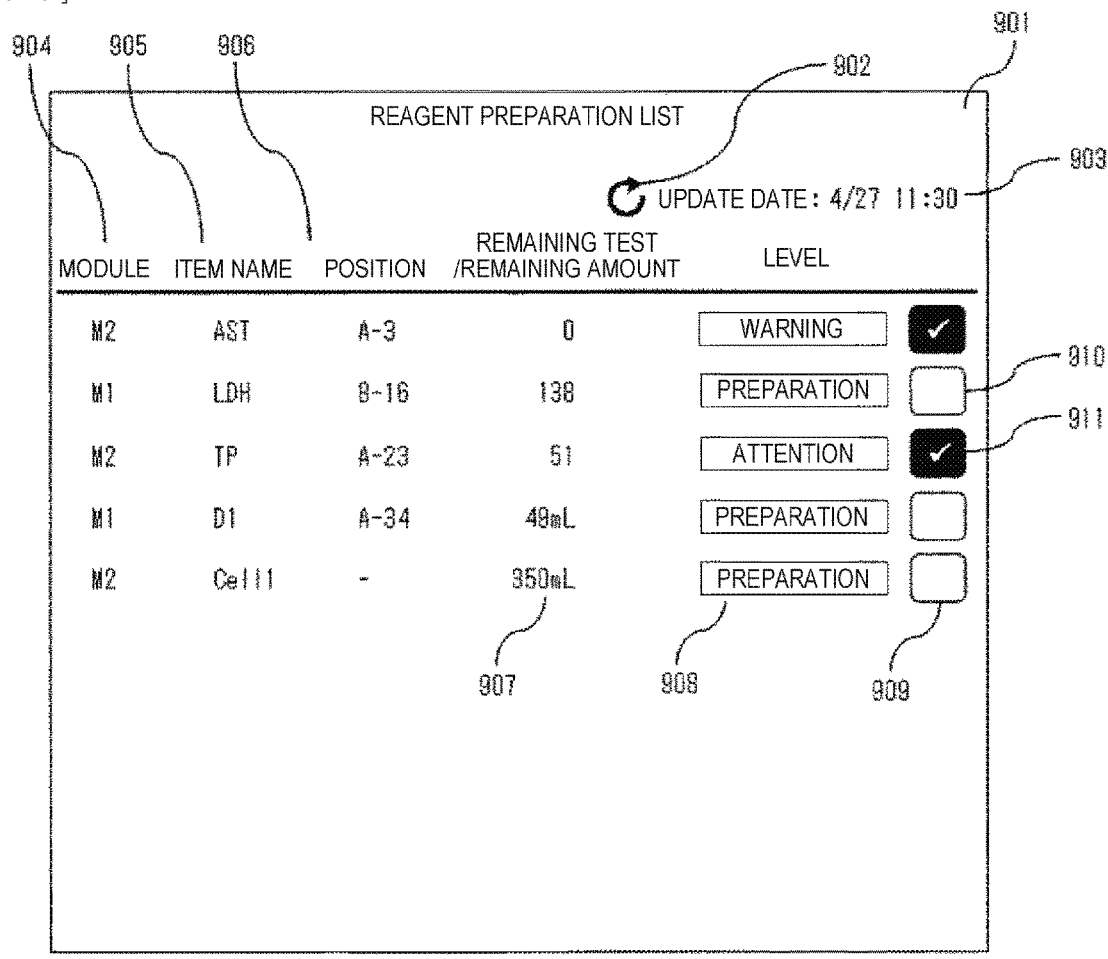

[FIG. 10]

| MODULE | ITEM NAME | POSITION | REMAINING TEST /REMAINING AMOUNT | LEVEL | |
|--------|-----------|----------|-----------------------------------|-------------|----|
| M2 | AST | A-3 | 0 | WARNING | NG |
| M1 | LDH | B-16 | 138 | PREPARATION | |
| M2 | TP | A-23 | 51 | ATTENTION | NG |
| M1 | D1 | A-34 | 49mL | PREPARATION | |
| M2 | Cell | - | 350mL | PREPARATION | |

REAGENT PREPARATION LIST

UPDATE DATE : 4/27 11:30

[FIG. 11]

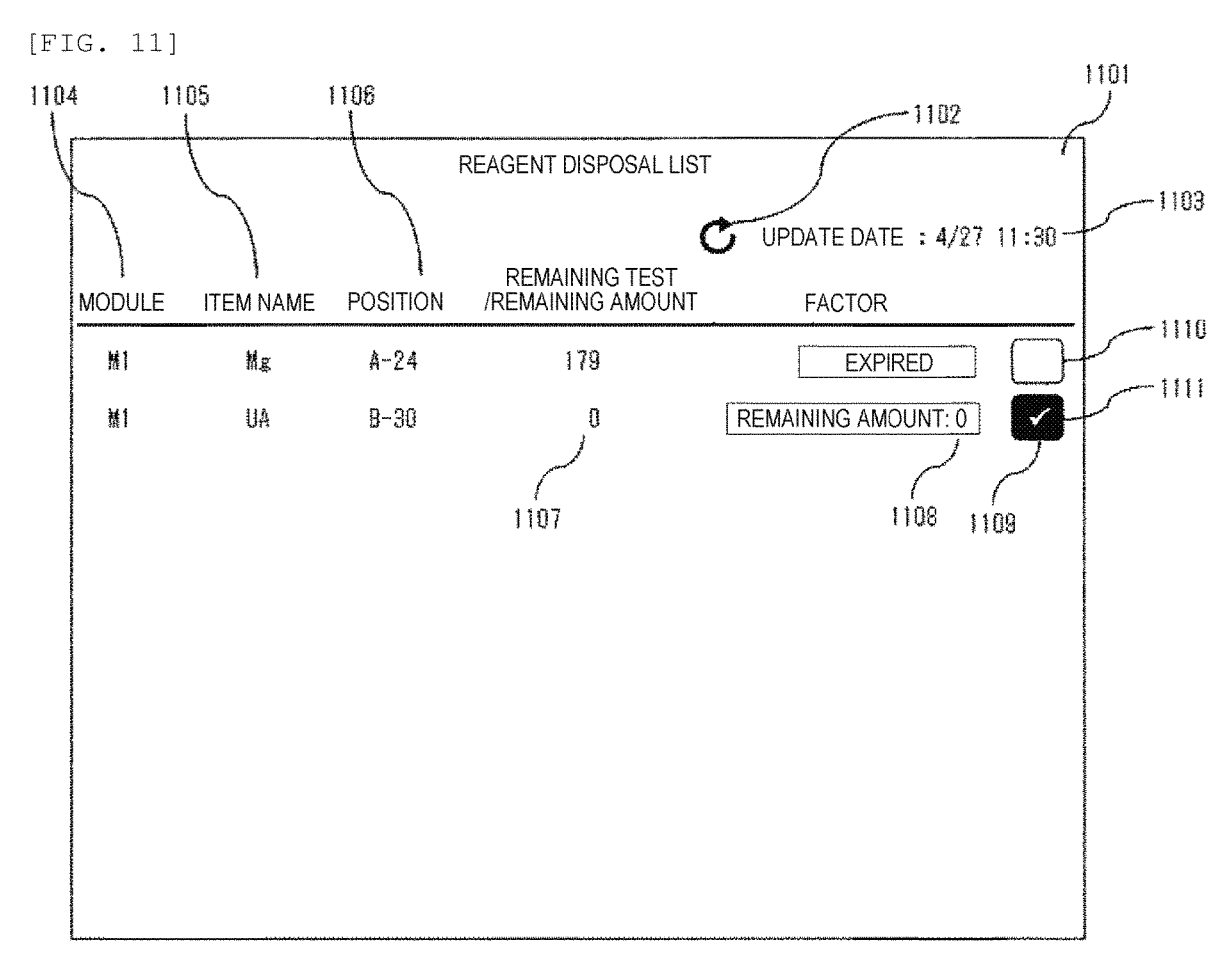

REAGENT DISPOSAL LIST

UPDATE DATE : 4/27 11:30

| MODULE | ITEM NAME | POSITION | REMAINING TEST /REMAINING AMOUNT | FACTOR | |
|---|---|---|---|---|---|
| M1 | Mg | A-24 | 179 | EXPIRED | ☐ |
| M1 | UA | B-30 | 0 | REMAINING AMOUNT: 0 | ✓ |

[FIG. 12]
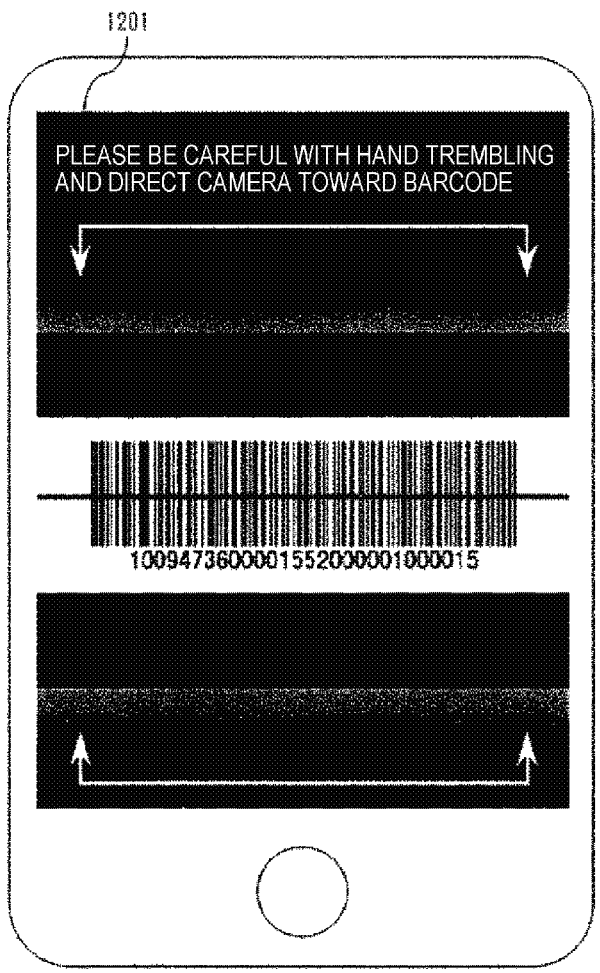

[FIG. 13]
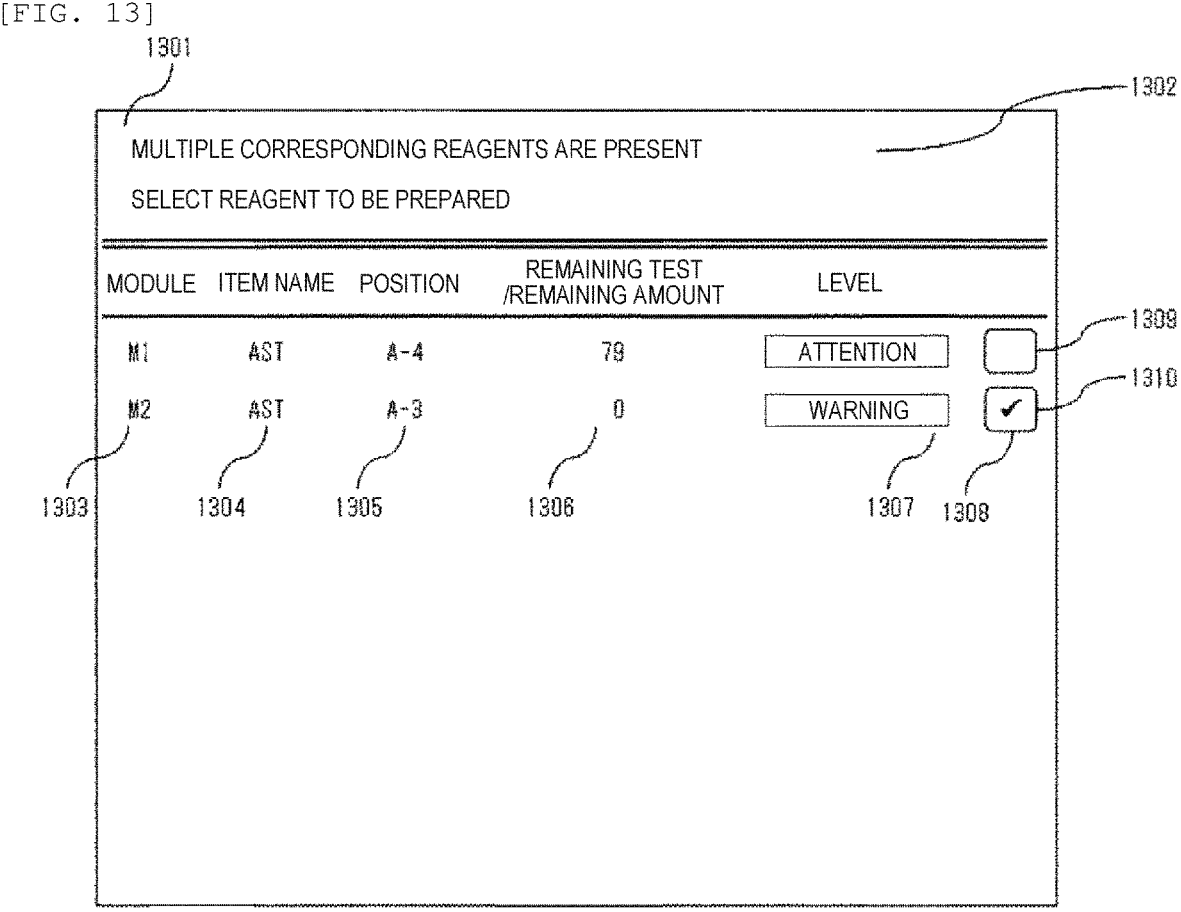

[FIG. 14]
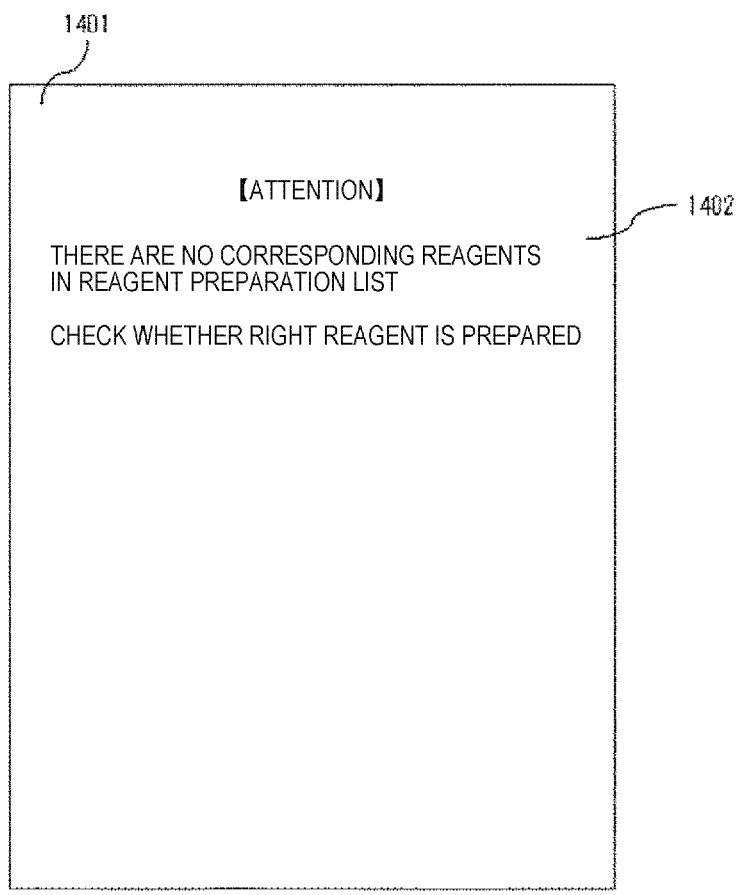

AUTOMATIC ANALYZER, AUTOMATIC ANALYSIS SYSTEM, AND DISPLAY METHOD OF REAGENT LIST

TECHNICAL FIELD

The present invention relates to an automatic analyzer that performs qualitative and quantitative analysis of biological samples such as blood and urine.

BACKGROUND ART

In an automatic analyzer that performs qualitative and quantitative analysis of a specific component included in a biological sample (hereinafter, simply referred to as "sample") such as blood or urine by using the sample and a reagent, typically, a series of preparation operations such as an operation of checking the remaining amounts of reagents to be used on the day, an operation of refilling a reagent whose remaining amount is insufficient, or an operation adding a new reagent container, are performed before measuring the sample. An operation of disposing a used-up reagent container is also performed.

To simplify the reagent preparation operation or the reagent disposal operation, typically, an automatic analyzer has a function of setting a threshold for the reagent remaining amount per analytic item. In addition, it has a function of outputting, on a screen or paper, only reagents whose remaining amounts are less than the threshold, as a reagent preparation list or a reagent disposal list.

For example, JP-A-2015-163896 (PTL 1) discloses a technique of issuing a warning to an operator through a screen or the like when the reagent remaining amount is less than a preset threshold.

CITATION LIST

Patent Literature

PTL 1: JP-A-2015-163896

SUMMARY OF INVENTION

Technical Problem

For example, in a large-sized automatic analyzer, when an operation of preparing a reagent whose remaining amount is insufficient or an operation of disposing a reagent whose remaining amount is zero is performed, an operation unit and an analyzing unit where a reagent container is set may be distant from each other such that it is difficult to prepare/dispose a reagent while checking an operation screen. In this case, a reagent preparation/disposal list is printed on paper, and the operation is performed while looking at the preparation/disposal list in many cases. However, e and labor is required for printing operation, and the costs for paper and ink are also generated. This technique is also advantageous in that, by printing the preparation/disposal list on paper, the operation can be performed while putting a check mark on a reagent to be actually prepared/disposed, with a pencil or the like, and thus has been used in a real operation.

The present invention has been made in consideration of the above-described circumstances, and an object thereof is to provide an automatic analyzer that can perform a reagent preparation/disposal operation comfortably and smoothly as when printing a reagent preparation/disposal list on paper even without printing the reagent preparation/disposal list.

Solution to Problem

A representative solving means of the present application is as follows. Provided is an automatic analyzer including: a reagent container setting unit on which a plurality of reagent containers are set; a reagent dispensing mechanism that aspirates a reagent from each of the reagent containers set on the reagent container setting unit; a reagent managing unit that manages information related to the reagent of each of the reagent containers set on the reagent container setting unit; a storage unit that stores reagent information related to a reagent remaining amount or a reagent expiration date of each of the reagent containers set on the reagent container setting unit; and a display unit that displays a reagent list in which reminder information that gives a reminder to an operator is assigned to each of setting positions of the reagent containers, based on the reagent information stored in the storage unit, in which the reagent managing unit updates display of the reagent list such that a reagent container selected by the operator is visually identifiable while the reagent list is displayed.

Another representative solving means is as follows. Provided is a display method of a reagent list of an automatic analyzer, the automatic analyzer including a reagent container setting unit on which a plurality of reagent containers are set, a reagent dispensing mechanism that aspirates a reagent from each of the reagent containers set on the reagent container setting unit, a reagent managing unit that manages information related to the reagent of each of the reagent containers set on the reagent container setting unit, a storage unit that stores reagent information related to a reagent remaining amount or a reagent expiration date of each of the reagent containers set on the reagent container setting unit. This display method includes: receiving selection of a reagent container from an operator through a display unit that displays a reagent list in which reminder information that gives a reminder to the operator is assigned to each of setting positions of the reagent containers, based on the reagent information stored in the storage unit; and causing the display unit to update display of the reagent list such that the reagent container selected by the operator is visually identifiable while the reagent list is displayed.

Advantageous Effects of Invention

According to the present invention, a reagent preparation/disposal operation can be performed comfortably and smoothly as when printing a reagent preparation/disposal list on paper even without printing the reagent preparation/disposal list. As a result, the time and labor required for printing the reagent preparation/disposal list can be saved, and the costs for paper and ink can be saved.

BRIEF DESCRIPTION OF DRAWINGS

FIG. 1 is a diagram schematically illustrating an overall configuration of an automatic analyzer according to an embodiment of the present invention.

FIG. 2 is a functional block diagram illustrating an operating unit PC and a tablet terminal.

FIG. 3 is a diagram illustrating a reagent preparation list screen of the tablet terminal (before a consistency check; and an example in which a mark is a check mark).

FIG. 4 is a diagram illustrating a reagent preparation list screen of the tablet terminal (before the consistency check; and an example in which a mark is OK).

FIG. 5 is a diagram illustrating a reagent disposal list screen of the tablet terminal (before the consistency check; and an example in which a mark is a check mark).

FIG. 6 is a sequence diagram illustrating information exchange between the automatic analyzer and the tablet terminal per event.

FIG. 7 is a flowchart illustrating the contents of a consistency check process of reagent preparation during a reagent remaining amount registration event in the automatic analyzer.

FIG. 8 is a flowchart illustrating the contents of a consistency check process of reagent disposal during the reagent remaining amount registration event in the automatic analyzer.

FIG. 9 is a diagram illustrating a reagent preparation list screen of the tablet terminal (after the consistency check; and an example in which a mark is a check mark).

FIG. 10 is a diagram illustrating a reagent preparation list screen of the tablet terminal (after the consistency check; and an example in which a mark is NG).

FIG. 11 is a diagram illustrating a reagent disposal list screen of the tablet terminal (after the consistency check; and an example in which a mark is a check mark).

FIG. 12 is a diagram illustrating a barcode-reading camera screen of the tablet terminal.

FIG. 13 is a diagram illustrating a reagent selection screen of the tablet terminal displayed when multiple corresponding reagents are present during reagent barcode reading.

FIG. 14 is a diagram illustrating an attention screen of the tablet terminal displayed when the corresponding reagent is not present during the reagent barcode reading.

DESCRIPTION OF EMBODIMENTS

Hereinafter, an embodiment of the present invention will be described with reference to the drawings.

FIG. 1 is a diagram schematically illustrating an overall configuration of an automatic analyzer according to the embodiment.

In FIG. 1, roughly, an automatic analyzer 100 includes a sample loading unit 104, analyzing units 106a, 106b, and 106c, a sample housing unit 109, a transport line 105, an operating unit PC 111, and a tablet terminal 114.

A sample as an analysis target is contained in a sample container 102, plural sample containers 102 are loaded on a sample rack 103, and the sample rack 103 is loaded on the sample loading unit 104. This sample loading unit 104 is connected to the sample housing unit 109 that houses the sample rack 103 through the transportation line 105 through which the sample rack 103 is transported. One or more (for example, in the embodiment, three) analyzing units 106a, 106b, and 106c are disposed along the transportation line 105.

The operating unit PC 111 controls an overall operation of the automatic analyzer 100 and is connected to respective configurations of the automatic analyzer 100 through a communication device 110 (for example, a hub). The operating unit PC 111 is connected to a wireless device 113 (for example, a wireless router) and is communicably connected to the tablet terminal 114 by wireless communication. The operating unit PC 111 is also connected to a higher-level host system 112 that controls an overall operation of an analysis system including the automatic analyzer 100.

A sample as an analysis target is contained in the sample container 102, plural sample containers 102 are loaded on the sample rack 103, and the sample rack 103 is loaded on the sample loading unit 104. This sample loading unit 104 is transported to each of the analyzing units 106a, 106b, and 106c, the sample housing unit 109, or the like through the transportation line 105. Examples of the sample contained in the sample container 102 include a calibration sample used for calibration measurement, a precision control sample used for precision control measurement, and a patient sample that is a biological sample such as blood or urine. In each of the sample containers 102 mounted on the sample rack 103, a tag 102a (for example, a barcode or a RFID) for identifying the sample to be contained is provided. Identification information is read by a reading device (not illustrated) and transmitted to the operating unit PC 111 or the like.

For example, the analyzing unit 106a includes: a reaction disk 120a that includes plural reaction containers; a sample dispensing mechanism 121a that dispenses the sample contained in the sample container 102 into the reaction container, the sample container 102 being transported through the transportation line 105; a reagent disk 108a (reagent container mounting unit) on which plural reagent containers 107 each of which contains a reagent used for analyzing the sample are set; a reagent dispensing mechanism 122a that aspirates the reagent of the reagent container 107 set on the reagent disk and dispenses the aspirated reagent into the reaction container; and a photometric mechanism 123a that measures an absorbance, a scattered light intensity, or the like of a mixed solution (reaction solution) of the sample and the reagent contained in the reaction container. The analyzing unit 106a analyzes optical information obtained from the photometric mechanism 123a such that the content or the like of a predetermined material in the sample can be analyzed. For example, the analyzing units 106b and 106c have the same configuration as the analyzing unit 106a, and include reaction disks 120b and 120c, sample dispensing mechanisms 121b and 121c, reagent disks 108b and 108c, reagent dispensing mechanisms 122b and 122c, and photometric mechanisms 123b and 123c, respectively.

The tablet terminal 104 is communicably connected to the operating unit PC 111 through the wireless device 113. An operator 101 can see each information of the automatic analyzer 100 from a screen of the tablet terminal 104.

FIG. 2 is a functional block diagram illustrating the operating unit PC and the tablet terminal.

FIG. 2 illustrates when information exchanges between the operating unit PC 111 and the tablet terminal 114 by communication 203 through the wireless device 113.

In FIG. 2, for example, the operating unit PC 111 includes an input unit 201, a display unit 202, a reagent managing unit 204, a to-terminal communication unit 205, a storage unit 206, and a to-analyzing unit communication unit 207. The operating unit PC 111 communicates with an analyzing unit 200 (for example, the sample loading unit 104, the analyzing unit 106a, 106b, or 106c) of another configuration of the automatic analyzer 100.

The input unit 201 is, for example, a keyboard or a mouse and performs, for example, the pressing (mouse-clicking) of buttons on various operation screens displayed on the display unit 202 using a mouse cursor or the input of numbers or characters into an input frame using a keyboard. That is, the input unit 201 and the display unit 202 configure a graphical use interface (GUI).

The reagent managing unit 204 manages information related to the reagents of the reagent containers 107 or the like set on the reagent disks 108a, 108b, 108c of the analyzing unit 200. Specifically, the reagent managing unit 204 performs association with an analytic item, remaining amount management, usage priority management when plural reagent containers 107 are set for one analytic item, reagent expiration date management, and the like. When a new reagent container 107 is set, the reagent managing unit 204 searches cumulative reagent information stored in the storage unit 206 to determine whether the same reagent container is previously set. When the same reagent container is previously set, the reagent information stored in the storage unit 206 is extracted. When the same reagent container is not previously set, the reagent managing unit 204 manages the set reagent container as a new reagent container 107. In the remaining amount management, the reagent managing unit 204 also performs a process of registering a reagent whose remaining amount is less than a threshold for the remaining amount set per analytic item through the input unit 201 in a reagent preparation list or a reagent disposal list. The reagent managing unit 204 can perform, for example, control related to the display of the display unit 202.

The to-terminal communication unit 205 performs control of wireless communication with the tablet terminal 114, generation of a communication text to be transmitted to the tablet terminal 114, and distribution of information of a communication text received from the tablet terminal 114.

The storage unit 206 stores information required for the management in the reagent managing unit 204 and stores reagent information related to a reagent remaining amount or a reagent expiration date of the reagent containers set on the reagent disk 108a.

The to-analyzing unit communication unit 207 performs control of communication with the analyzing unit 200, generation of a communication text to be transmitted to the analyzing unit 200, and distribution of information of a communication text received from the analyzing unit 200.

In FIG. 2, for example, the tablet terminal 114 includes a terminal display unit 208, a terminal communication unit 209, a terminal reagent managing unit 210, and a terminal input unit 211. The tablet terminal 114 communicates with the operating unit PC 111 through the wireless device 113 such that various information can be achieved from the automatic analyzer 100 or an operation of the automatic analyzer 100 can be performed.

In the tablet terminal 114, like the operating unit PC 111, a GUI is configured by the terminal display unit 208 and the terminal input unit 211 such that various kinds of information (including information of the reagent preparation/disposal list) transmitted from the operating unit PC 111 is received and displayed on the terminal display unit 208 or an operation instruction or the like is input to the automatic analyzer 100 through the terminal input unit 211 and is transmitted to the operating unit PC 111.

The terminal communication unit 209 performs control of wireless communication with the operating unit PC 111, generation of a communication text to be transmitted to the operating unit PC 111, and distribution of information of a communication text received from the operating unit PC 111.

The terminal reagent managing unit 210 performs management of information (including information of the reagent preparation/disposal list) related to the reagent received from the operating unit PC 111, management of information of a mark input from the terminal input unit 211, and the like. When one tablet terminal 114 is wirelessly connected to operating unit PCs 111 of plural automatic analyzers 100, the terminal reagent managing unit 210 performs total management of the reagent information of the automatic analyzers 100.

FIG. 3 illustrates an example of a reagent preparation list screen of the tablet terminal, in which the display of a mark is a check mark.

The reagent preparation list refers to a list for an operator to prepare a reagent. With this reagent preparation list, the operator can easily understand which reagent is insufficient, and can determine a reagent to be newly set. The storage unit 206 stores the reagent remaining amount information of all the reagent containers set on the reagent disks (for example, 108a). In the reagent preparation list, however, reagent containers in which the reagent remaining amount is insufficient are particularly selected from the all the reagent containers and are listed. That is, the reagent preparation list shows a list of reagent containers in which the reagent remaining amount is less than or equal to a predetermined threshold, based on the reagent remaining amount stored in the storage unit.

The reagent remaining amount can be achieved using, for example, a technique in which the reagent remaining amount is specified by detecting a liquid level, based on a change in capacitance when a nozzle included in the reagent dispensing mechanism has been lowered and reached the liquid level, or a technique in which the nozzle is lowered by a predetermined amount, the reagent is aspirated through the nozzle, it is judged whether the nozzle has reached a liquid level based on a pressure value that is detected by a pressure sensor included in the reagent dispensing mechanism, and the reagent remaining amount is specified based on the liquid level.

On the reagent preparation list screen 301 of the tablet terminal illustrated in FIG. 3, basically, the same information as the reagent preparation list information displayed on the display unit 202 of the operating unit PC 111 or the reagent preparation list information that is printed on paper by a printer connected to the operating unit PC 111 is displayed, and information such as a module name 304, an analytic item name 305, a reagent container setting position 306, a reagent remaining amount information (the number of remaining tests or the remaining amount) 307, and a level 308 indicating the degree to which the remaining amount is less than the threshold is displayed. The meaning of the reagent remaining amount described herein includes not only the remaining amount but also the number of remaining tests.

These types of information can be reading, using a reading device (a bar code reader or a RFID reading device) in the reagent disk reading, a barcode or an RFID attached to the reagent container.

The storage unit stores in advance, information as to at which module, at which reagent disk, and at which position the reagent is arranged, and which analytic item the reagent has. Accordingly, these types of information can be easily arranged in a list.

The reagent remaining amount information in the storage unit can be updated and easily listed, without measuring the reagent remaining amount every time, by subtracting, from the original remaining amount information, a value that is calculated in consideration of the number of times of analysis, the reagent amount used for single analysis, and the like.

The reagent remaining amount information can be listed by any one of the reagent managing unit 204 and the terminal reagent managing unit 210.

Regarding the level 308, in the example of FIG. 3, two levels of thresholds can be set. "Preparation" is displayed for the reagent container 107 in which the remaining amount is less than the first level of threshold, "Attention" is displayed for the reagent container 107 in which the remaining amount is less than the second level of threshold that is less than the first level, and "Warning" is displayed for the reagent container 107 in which the remaining amount is zero. The level 308 corresponds to reminder information that gives a reminder that urges attention of an operator, and is displayed in the reagent preparation list for each of setting positions of the reagent containers, based on the reagent remaining amount stored in the storage unit. The reagent managing unit 204 or the terminal reagent managing unit 210 determines the level by comparing the reagent remaining amount and the threshold. The threshold is stored in the storage unit. As described above, it is desirable that the reminder information is information indicating multiple reminder levels such as "Preparation", "Attention", and "Warning" according to the degree of the reagent remaining amount. The reason for this is that the information indicating the reminder level is useful for determining the priority of the reagent container to be prepared.

The tablet terminal is a touch panel type display unit, and a mark button 309 switches between a marked state and an unmarked state when tapped on the screen. FIG. 3 illustrates an example in which the display of a mark is a check mark. An unmarked mark button 310 is switched to a marked mark button 311 when tapped. Likewise, the marked mark button 311 is switched to the unmarked mark button 310 when tapped. By using the display switching function of the mark button 309, the same operation as the operation of putting a check mark on the reagent preparation list printed on paper with a pencil or the like can be realized, and the preparation operation of the reagent container 107 can be smoothly performed.

When an update button 302 is pressed, the information on the module display portion 304 to the mark button display portion 309 that is displayed on the reagent preparation list screen 301 are updated to the latest information.

The update date display portion 303 displays, when the information on the module display portion 304 to the mark button display portion 309 displayed on the reagent preparation list screen 301 is updated, in units of minutes.

In this way, the terminal reagent managing unit 210 can change display of the reagent list such that a reagent container selected by the operator is visually identifiable while the reagent preparation list is displayed. The display of the reagent preparation list is updated when tapped by the operator.

FIG. 4 illustrates an example of a reagent preparation list screen of the tablet terminal, in which the display of a mark is "OK".

A difference between a reagent preparation list screen 401 of the tablet terminal of FIG. 4 and the reagent preparation list screen 301 of FIG. 3 is a marked mark button 411, which is "OK" instead of a check mark. An unmarked mark button 410 is switched to the marked mark button 411 when tapped. Likewise, the marked mark button 411 is switched to the unmarked mark button 410 when tapped.

The other reference numerals 402 to 408 are the same as the reference numerals 302 to 308 of FIG. 3.

That is, "OK" may be used instead of the marked mark button of FIG. 3, and the means is not particularly limited as long as it is a method in which the operator can visually recognize the display. For example, a method of changing the color of a tapped position or displaying a tapped position in a bold style to visually identify the tapped position may be adopted, instead of providing a box as illustrated in FIGS. 3 and 4. The terminal reagent managing unit 210 may be configured to judge, when the operator taps the screen, the reagent container selected by the operator. Then, the display of the reagent preparation list may be updated, such that the reagent container is visually identifiable.

As illustrated in FIGS. 3 and 4, the reagent preparation list includes the mark button for each of the setting positions of the reagent containers, and the terminal reagent managing unit 210 switches the display between the marked mark button and the unmarked mark button by detecting the tapping of the operator on the mark button. This visual identification using the switching is effective in terms of visibility.

Even when the tablet terminal is not a touch panel type, the same operation can be realized by providing physical buttons. Although use of physical buttons is not excluded from the present invention, it is desirable to select a touch panel type display in terms of convenience.

FIG. 5 illustrates an example of a reagent disposal list screen of the tablet terminal in which the display of a mark is a check mark.

The reagent disposal list refers to a list for the operator to dispose a reagent. With this reagent disposal list, the operator can easily understand where the reagent container to be extracted from the reagent disk is located. The storage unit 206 stores the information related to the reagent remaining amounts and the expiration dates of all the reagent containers set on the reagent disks (for example, 108*a*). In the reagent disposal list, however, reagent containers in which the reagent remaining amount is zero and reagent containers in which the reagent expiration date is expired are particularly selected from the all the reagent containers and are listed. These reagent containers should be extracted from the viewpoint of securing empty positions of the reagent disks. That is, the reagent disposal list is a reagent disposal list that shows a list of reagent containers in which the reagent remaining amount is zero and reagent containers in which the reagent expiration date is expired, based on the information related to the reagent remaining amount and the reagent expiration date stored in the storage unit.

On the reagent disposal list screen 501 of the tablet terminal illustrated in FIG. 5, basically, the same information as the reagent disposal list information displayed on the display unit 202 of the operating unit PC 111 or the reagent disposal list information that is printed on paper by a printer connected to the operating unit PC 111 is displayed, and information such as a module name 504, an analytic item name 505, a reagent container setting position 506, a reagent remaining amount information (the number of remaining tests or the remaining amount) 507, and a disposal factor ("Remaining Amount: 0" or "Expired") 508 is displayed.

As the reminder information that gives a reminder to the operator, the reason of the disposal is displayed. However, unlike the reagent preparation list, the reason of disposal is not quantifiable. Therefore, it is desirable to show the reasons such as "Remaining Amount: 0" or "Reagent Expiration date Expired" as the reminder information.

A mark button 509 switches between a marked state and an unmarked state when tapped on the screen. FIG. 5 illustrates an example in which the display of a mark is a check mark, and an unmarked mark button 510 is switched to a marked mark button 511 when tapped. Likewise, the marked mark button 511 is switched to the unmarked mark button 510 when tapped. By using the display switching function of the mark button 509, the same operation as the operation of putting a check mark on the reagent disposal list printed on paper with a pencil or the like can be realized, and the disposal operation of the reagent container 107 can be smoothly performed.

When an update button 502 is pressed, the information displayed on the module display portion 504 to the mark button display portion 509 of the reagent disposal list screen 501 are updated to the latest information.

The update date display portion 503 displays, when the information on the module display portion 504 to the mark button display portion 509 displayed on the reagent disposal list screen 501 is updated, in units of minutes.

The description of the reagent preparation list is the same as that of the reagent disposal list, and thus will not be repeated.

Next, the flow of the information displayed on the reagent preparation list screens 301 and 401 and the reagent disposal screen 501 of the tablet terminal in the automatic analyzer according to the embodiment will be described.

FIG. 6 is a sequence diagram illustrating information exchange between the automatic analyzer and the tablet terminal per event.

When a device start event 603 occurs, the automatic analyzer 601 generates (604) reagent preparation/disposal list information and transmits the generated reagent preparation/disposal list information 605 to a tablet terminal 602. The generation of the information is performed by the reagent managing unit 204.

Even when an event 606 of consuming a reagent such as an analysis operation of a sample or a preparation operation thereof occurs, the automatic analyzer 601 generates (607) reagent preparation/disposal list information and transmits the generated reagent preparation/disposal list information 608 to the tablet terminal 602. The generation of the information is performed by the reagent managing unit 204.

If the mark buttons 309, 409, and 509 of the reagent preparation list screens 301 and 401 and the reagent disposal screen 501 of the tablet terminal 602 are tapped, a marking event 609 occurs. The marking event 609 puts a mark on the prepared reagents or on the disposed reagents. In the marking event 609, the tablet terminal 602 generates (610) information of the marked reagents, and transmits the information 611 of the marked reagents to the automatic analyzer 601. The generation of the information is performed by the terminal reagent managing unit 210.

In the processes up to the generation 610 of the information, the screens illustrated in FIGS. 3 to 5 can be displayed. With this screen display, the preparation or disposal of the reagents can be smoothly performed. Next, useful functions will be further described.

Next, information exchange when a reagent remaining amount registration event 612 occurs will be described. The reagent remaining amount registration refers to an operation of registering the reagent information and the remaining amount information of the reagent containers 107 set in the reagent disks 108a, 108b, and 108c in the automatic analyzer (storing the information in the storage unit 206 of the operating unit PC 111). The reagent information is registered, for example, by reading the information from a barcode or an RFID attached to the reagent container 107 or by manually inputting the information through the input unit 201 of the operating unit PC 111. The remaining amount information is registered, for example, by calculating the information, based on the liquid level of the reagent detected by a liquid level detecting function of the nozzle provided in the reagent dispensing mechanism 122a, 122b, and 122c or by manually inputting the information through the input unit 201 of the operating unit PC 111.

When the reagent remaining amount registration event 612 occurs, the automatic analyzer 601 generates (613) the reagent preparation/disposal list information, based on the registered reagent information and the registered remaining amount information. The consistency of the reagent preparation/disposal list information is checked, and the check result is generated (614). The consistency check of the reagent preparation/disposal list information is a function that has not been described in this disclosure, and thus will be described hereinbelow. This function is a function of checking whether the reagents that are marked on the reagent preparation list screens 301 and 401 and the reagent disposal screen 501 of the tablet terminal 602 are actually prepared/disposed, based on the information 611 of the marked reagents transmitted from the tablet terminal 602 and the reagent information and the remaining amount information registered through the reagent remaining amount registration operation. In the consistency check of the reagent preparation list information, if the remaining amount of the newly set reagent container 107 is less than the threshold for the remaining amount preset per analytic item through the input unit 201 of the operating unit PC 111, judgment of "abnormal" is done. The details of the process flow of the consistency check of the reagent preparation/disposal list information will be described below in the description of FIGS. 7 and 8.

The generated reagent preparation/disposal list information and consistency check result information 615 of the reagent preparation/disposal list information are transmitted to the tablet terminal 602. The generation of the check result information is performed by the reagent managing unit 204.

FIG. 7 is a flowchart illustrating the contents of the consistency check process of the reagent preparation during the above-described reagent remaining amount registration event in the automatic analyzer, in which the process corresponding to one reagent container 107 is illustrated. This flow is performed by the reagent managing unit 204.

When the consistency check process of the reagent preparation is started, "OK" is initially set to a variable "Consistency Check Result" (Step S701). Next, whether the reagent remaining amount of the reagent container 107 registered through the reagent remaining amount registration operation is less than the threshold for the remaining amount set per analytic item through the input unit 201 of the operating unit PC 111 is determined (Step S702). When the determination result is "NO", the process ends. When the determination result is "YES", whether the reagent container 107 is marked on the reagent preparation list screens 301 and 401 of the tablet terminal 602 is determined (Step S703). When the determination result is "YES", "NG" is set to the variable "Consistency Check Result" (Step S705), and the process ends. When the determination result is "NO", whether the reagent container 107 is newly set on the automatic analyzer 601 is determined (Step S704). For the determination on whether the reagent container 107 is new, the cumulative reagent information stored in the storage unit 206 of the operating unit PC 111 is used. When the determination result is "NO", the process ends. When the determination result is "YES", "NG" is set to the variable "Consistency Check Result" (Step S705), and the process ends. The determination result of the consistency check process of the reagent preparation is transmitted to the tablet terminal 602.

FIG. 8 is a flowchart illustrating the contents of the consistency check process of the reagent disposal during the above-described reagent remaining amount registration event in the automatic analyzer, in which the process corresponding to one reagent container 107 is illustrated.

When the consistency check process of the reagent disposal is started, "OK" is initially set to a variable "Consistency Check Result" (Step S801). Next, whether the reagent container 107 is marked on the reagent disposal list screen 501 of the tablet terminal 602 is determined (Step S802). When the determination result is "NO", the process ends. When the determination result is "YES", "NG" is set to the variable "Consistency Check Result" (Step S803), and the process ends. The determination result of the consistency check process of the reagent disposal is transmitted to the tablet terminal 602.

FIG. 9 illustrates an example of a reagent preparation list screen of the tablet terminal after the consistency check of the reagent preparation, in which the display of a mark is a check mark.

In the mark button display portion 909, the reagent container 107 in which the consistency check result of the reagent preparation is OK is displayed by an unmarked mark button 910, and the reagent container 107 in which the consistency check result of the reagent preparation is NG is displayed by a marked mark button 911. The marked mark button 911 and the marked mark button 311 have different designs so as to identify a visual difference therebetween, the marked mark button 311 being a mark button when the unmarked mark button 910 is tapped (in the embodiment, the tapped marked mark button 311 is displayed such that the check mark is black and the background is white, and the marked mark button 911 in which the consistency check result is NG is displayed such that the check mark is white and the background is black). As a result, reagents that are forgotten to be prepared on the reagent preparation list screen 901 of the tablet terminal 602 are visually identifiable, and the risk of starting analysis without noticing reagents that are forgotten to be prepared can be reduced.

The other reference numerals 902 to 908 are the same as the reference numerals 302 to 308 of FIG. 3.

FIG. 10 illustrates an example of a reagent preparation list screen of the tablet terminal after the consistency check of the reagent preparation, in which the display of a mark is "NG".

A difference between a reagent preparation list screen 1001 of the tablet terminal of FIG. 10 and the reagent preparation list screen 901 of FIG. 9 is a marked mark button 1011, which is "NG".

The other reference numerals 1002 to 1008 are the same as the reference numerals 902 to 908 of FIG. 9.

In this way, when the reagent remaining amount registration is performed, the reagent managing unit 204 determines whether reagent remaining amounts of reagents corresponding to the same analytic item as the reagent container selected by the operator are less than or equal to the predetermined threshold, and displays the determination result on the reagent preparation list. This threshold may be, for example, a threshold based on the remaining amount before reagent remaining amount registration instead of the threshold of the level 308 and may be freely set. When an operation other than a manual input is performed in the reagent remaining amount registration, an instruction of the operator is a prerequisite. The reagent managing unit 204 can cause the reagent dispensing mechanism to automatically perform a remaining amount check operation on each of the reagent containers set on the reagent disk based on the instruction. In this way, the reagent managing unit 204 can also indirectly control the reagent dispensing mechanism.

FIG. 11 illustrates an example of a reagent disposal list screen of the tablet terminal after the consistency check of the reagent disposal, in which the display of a mark is a check mark.

In the mark button display portion 1109, the reagent container 107 in which the consistency check result of the reagent disposal is OK is displayed by an unmarked mark button 1110, and the reagent container 107 in which the consistency check result of the reagent preparation is NG is displayed by a marked mark button 1111. The marked mark button 1111 and the marked mark button 511 have different designs so as to identify a visual difference therebetween, the marked mark button 511 being a mark button when the unmarked mark button 1110 is tapped. As a result, reagents that are forgotten to be disposed on the reagent disposal list screen 1101 of the tablet terminal 602 are visually identifiable, and the risk of starting analysis without noticing reagents that are forgotten to be disposed can be reduced.

When the reagent remaining amount registration is automatically is performed based on the instruction of the operator as a prerequisite, not only the remaining amount of the reagent container but also whether the reagent container is present can be checked. Therefore, the reagent managing unit 204 determines whether the reagent container selected by the operator is extracted from the reagent container setting unit, and displays the determination result on the reagent disposal list.

The meaning of the instruction of the operator include not only a direct instruction of performing only the reagent remaining amount registration but also an indirect instruction such as the reagent remaining amount registration that is performed at the start of analysis.

FIG. 12 is a diagram illustrating a barcode-reading camera screen of the tablet terminal.

FIG. 12 illustrates a screen when a barcode attached to the reagent container 107 is about to be read by a barcode-reading camera function provided in the tablet terminal 602.

With this function, reagents to be prepared/disposed can be automatically marked, in addition to the above-described marking that is performed when the mark buttons 309, 409, and 509 of the reagent preparation list screens 301 and 401 and the reagent disposal screen 501 of the tablet terminal 602 are tapped. This function can be realized by determining whether the reagent is to be prepared or to be disposed by starting any one of the reagent preparation list screen 301 and 401 and the reagent disposal screen 501, transmitting barcode information of the reagent read on the barcode-reading camera screen 1201 to the automatic analyzer 601, analyzing the barcode information with the reagent managing unit 204, and transmitting information of the position of the reagent container 107 to the tablet terminal 602. Due to this automation function, the risk of erroneously marking a reagent and erroneously preparing or disposing the reagent can be reduced as compared to the marking by the screen tapping.

In this way, when a tablet terminal includes a barcode-reading camera capable of reading a barcode attached to each of the reagent containers, the terminal reagent managing unit 210 can determine the reagent container selected by the operator based on barcode information attached to the reagent container that is read by the barcode-reading camera, and can update the display of the reagent preparation list or the reagent disposal list such that the reagent container selected by the operator is visually identifiable based on the determination result.

FIG. 13 is a diagram illustrating a reagent selection screen of the tablet terminal displayed when multiple corresponding reagents are present during the above-described reagent barcode reading.

When the barcode information of the reagent read on the barcode-reading camera screen 1201 is analyzed by the reagent managing unit 204 of the automatic analyzer 601, and if multiple corresponding reagent containers 107 are present, the information is received by the tablet terminal 602 and is displayed.

For example, regarding a reagent to be prepared, a message display portion 1302 displays "Multiple corresponding reagents are present. Select a reagent to be prepared" to urge the operator 101 to select the reagent.

On a module display portion 1303, an item name display portion 1304, a position display portion 1305, a remaining test/remaining amount display portion 1306, and a level display portion 1307, the corresponding information of all the reagent containers 107 are displayed, and the operator 101 taps a mark button 1308 of a reagent container 107 to be selected such that the reagent container 107 is selected. A display example of a mark button that is in a non-selected state is a mark button 1309. In an initial state, all the mark buttons are displayed as the mark buttons 1309. A display example of a mark button that is in a selected state is a mark button 1310. When the mark button 1309 of one reagent container 107 is tapped while another reagent container 107 is displayed with the mark button 1310, the display of the mark button of the tapped reagent container 107 is switched to the mark button 1310, and the display of the reagent container 107 that has been displayed with the mark button 1310 is switched to the mark button 1309. Next, by closing the reagent selection screen 1301, the button 309, 409, or 509 of the selected reagent container 107 is displayed by the marked mark button 311, 411, or 511 on the reagent preparation list screen 301 or 401 or the reagent disposal screen 501.

FIG. 14 is a diagram illustrating an attention screen of the tablet terminal displayed when there are no corresponding reagents present during the above-described reagent barcode reading.

When the barcode information of the reagent read on the barcode-reading camera screen 1201 is analyzed by the reagent managing unit 204 of the automatic analyzer 601, and if no corresponding reagent container 107 is not present, the information is received by the tablet terminal 602 and is displayed.

For example, in the case of a reagent to be prepared, a message display portion 1402 displays "There are no corresponding reagents in reagent preparation list. Check whether right reagent is prepared." to urge the operator 101 to check the reagent.

In the embodiment, the example where the reagent container setting unit is the reagent disk has been described. However, the reagent container setting unit is not necessarily a disk type. The above-described screen display is also applicable to a reagent container setting unit where reagent containers are set in a matrix in an X-Y direction. That is, the reagent container setting unit is not particularly limited as long as plural reagent containers are set therein.

In the embodiment, the example of the tablet terminal has been described. However, the display unit is not necessarily the tablet terminal, and the embodiment is also applicable to a display unit provided in the automatic analyzer. In this case, the display unit is not necessarily but desirably a touch panel type. The reason for this is that the operability is excellent. When the display unit provided in the automatic analyzer is adopted, in FIG. 2, the tablet terminal is not necessary, and the display unit provided in the automatic analyzer may exchange information with the display unit of the operating unit PC. That is, in the above description, the terminal reagent managing unit 210 may be simply replaced with the reagent managing unit 204.

An automatic analysis system including plural automatic analyzers may be installed in a laboratory. In this case, a tablet terminal may be connected to each of the automatic analyzers through a local network. Therefore, the tablet terminal can display the reagent preparation list or the reagent disposal list corresponding to each of the automatic analyzers.

In the case of the automatic analysis system, it is desirable that the tablet terminal switches displaying unit of the reagent preparation list or the reagent disposal list in units of the analysis modules, in units of the automatic analyzers, or in units of the automatic analysis system. When one analysis module is provided for one automatic analyzer, the display switches in units of the automatic analyzers or in units of the automatic analysis system. Therefore, to make the displaying unit switch in units of analysis modules, it is a prerequisite that any one of the automatic analyzers constituting the automatic analysis system includes plural analysis modules.

In the case of the automatic analysis system, a total reagent remaining amount of the same kind of reagents set on the reagent container setting units of the automatic analyzers may be displayed on the reagent preparation list. In addition, the reminder information may be information indicating a reminder level according to a degree of the total reagent remaining amount. As a result, the total remaining amount of all the reagents set on the automatic analyzers in the laboratory can be perceived. In this case, it is desirable that the display form of the reagent remaining amount list is different from that of FIG. 3 or the like, for example, a display form in which the reagent remaining amounts are aligned in units of analytic items and the positions of the plural reagent containers are displayed on the position item. It is desirable that the storage unit stores a threshold of the total reagent remaining amount for indicating the reminder level, the tablet terminal displays the reminder level on the reagent preparation list based on the threshold, and the threshold for the same reminder level is settable per day of the week. For example, the threshold for the level "Preparation" can be set to vary between Wednesday and Thursday. In a laboratory or the like, the operation state of an examination varies depending on the days of the week, and the preparation standard may vary depending on the days of the week.

The same display or operation can be performed even on a display unit not including an analyzing unit in a higher-level host or the like that controls the overall operations of the automatic analyzers. Therefore, a display method may be adopted, the display method including: displaying the reagent list such as the reagent preparation list or the reagent disposal list on the display unit of the higher-level host or the like; receiving selection of a reagent container from the operator through the display unit; and causing the display unit to update display of the reagent list such that the reagent container selected by the operator is visually identifiable while the reagent list is displayed. Since the reagent information is stored in the storage unit of the automatic analyzer, the display unit can display a reagent list in which reminder information that gives a reminder to the operator is assigned to each of setting positions of the reagent containers based on the reagent information stored in the storage unit of the automatic analyzer. However, in the display method, from the viewpoint of operability, it is more useful when the display unit is a touch panel type tablet terminal as in the embodiment instead of the display unit of the higher-level host or the like and receives selection of a reagent container that is performed by the operator tapping the reagent container, and the tablet terminal displays the reagent list such that the tapped reagent container is marked to be visually identifiable.

REFERENCE SIGNS LIST

100: automatic analyzer
101: operator
102: sample container
103: sample rack
104: sample loading unit
105: transport line
106a, 106b, 106c: analyzing unit
107: reagent container
108a, 108b, 108c: reagent disk
109: sample housing unit
110: communication device
112: higher-level host system
113: wireless device
114: tablet terminal
120a, 120b, 120c: reaction disk
121a, 121b, 121c: sample dispensing mechanism
122a, 122b, 122c: reagent dispensing mechanism
123a, 123b, 123c: photometric mechanism
200: analyzing unit
201: input unit
202: display unit
203: communication
204: reagent managing unit
205: to-terminal communication unit
206: storage unit
207: to-analyzing unit communication unit
208: terminal display unit
209: terminal communication unit
210: terminal reagent managing unit
211: terminal input unit
301: reagent preparation list screen
302: update button
303: update date display portion
304: module display portion
305: item name display portion
306: position display portion
307: remaining test/remaining amount display portion
308: level display portion
309: mark button display portion
310: mark button (unmarked)
311: mark button (marked)
401: reagent preparation list screen
402: update button
403: update date display portion
404: module display portion
405: item name display portion
406: position display portion
407: remaining test/remaining amount display portion
408: level display portion
409: mark button display portion
410: mark button (unmarked)
411: mark button (marked)
501: reagent disposal list screen
502: update button
503: update date display portion
504: module display portion
505: item name display portion
506: position display portion
507: remaining test/remaining amount display portion
508: factor display portion
509: mark button display portion
510: mark button (unmarked)
511: mark button (marked)
601: automatic analyzer
602: tablet terminal
901: reagent preparation list screen
902: update button
903: update date display portion
904: module display portion
905: item name display portion
906: position display portion
907: remaining test/remaining amount display portion
908: level display portion
909: mark button display portion
910: mark button (unmarked)
911: mark button (marked)
1001: reagent preparation list screen
1002: update button
1003: update date display portion
1004: module display portion
1005: item name display portion
1006: position display portion
1007: remaining test/remaining amount display portion
1008: level display portion
1009: mark button display portion
1010: mark button (unmarked)
1011: mark button (marked)
1101: reagent disposal list screen
1102: update button
1103: update date display portion
1104: module display portion
1105: item name display portion
1106: position display portion
1107: remaining test/remaining amount display portion
1108: factor display portion
1109: mark button display portion
1110: mark button (unmarked)
1111: mark button (marked)
1201: barcode-reading camera screen
1301: reagent selection screen
1302: message display portion
1303: module display portion
1304: item name display portion
1305: position display portion
1306: remaining test/remaining amount display portion
1307: level display portion
1308: mark button display portion
1309: mark button (unmarked)
1310: mark button (marked)
1401: attention screen
1402: message display portion

The invention claimed is:

1. An automatic analyzer comprising:
a reagent container setting unit on which a plurality of reagent containers are set;
a reagent dispensing mechanism that aspirates a reagent from each of the reagent containers set on the reagent container setting unit;
a computer coupled to a wireless device; and
a portable tablet terminal wirelessly coupled to the computer,
wherein the computer is programmed to:

manage information related to the respective reagents of each of the reagent containers set on the reagent container setting unit, and store reagent information related to a reagent remaining amount and a reagent expiration date of each of the reagent containers set on the reagent container setting unit, wherein the portable tablet terminal includes a touch panel display unit, wherein the portable tablet terminal is programmed to display a reagent list in which reminder information, which indicates a reminder to an operator, is assigned to each of a plurality of setting positions of particularly selected reagent containers among all of the reagent containers set on the reagent container setting unit based on the reagent information stored in the computer, the reagent list displaying information indicating the setting positions of each of the particularly selected reagent containers set on the reagent container setting unit, wherein the computer is programmed to update the display of the reagent list such that one or more of the particularly selected reagent containers among all of the reagent containers selected by the operator is visually identifiable while the reagent list is displayed, wherein the portable tablet terminal is programmed to upon receiving the selection of the one or more of the particularly selected reagent containers via the touch panel display unit of the reagent list displayed on the display unit, determine the one or more of the particularly selected reagent containers selected by the operator and update the display of the reagent list to add or remove a mark indicating and corresponding to the one or more of the particularly selected reagent containers, wherein the reagent list includes a plurality of individual mark buttons respectively corresponding to each of the particularly selected reagent containers and are displayed separate from the information indicating the setting positions of the particularly selected reagent containers and are areas of the displayed reagent list that are designated for displaying an indication of whether a respective mark is displayed or not displayed for each of the particularly selected reagent containers, each mark indicating the corresponding mark button has been tapped via the touch panel display unit of the portable tablet terminal, wherein the computer is programmed to switch display of each respective mark button between displaying the mark and not displaying the mark within the respective mark button of the displayed reagent list, wherein the computer is programmed to:

control the reagent dispensing mechanism and cause the reagent dispensing mechanism to automatically perform a remaining amount check operation on each of the particularly selected reagent containers among all of the reagent containers set on the reagent container setting unit, determine whether reagent remaining amounts of the reagents in the particularly selected reagent containers are less than or equal to a first predetermined threshold and determine whether reagent remaining amounts of the reagents in the particularly selected reagent containers are equal to or less than a second predetermined threshold, upon determining a respective amount of a reagent among the particularly selected reagent containers is less than or equal to the first predetermined threshold, display, in the reagent list, a first notification corresponding to the particularly selected reagent container in the reagent list that corresponds to the respective reagent, upon determining a respective amount of a reagent among the particularly selected reagent containers is less than or equal to the second predetermined threshold, display, in the reagent list, a second notification corresponding to the particularly selected reagent container in the reagent list that corresponds to the respective reagent, upon determining a respective amount of a reagent among the particularly selected reagent containers is zero, display, in the reagent list, a third notification corresponding to the particularly selected reagent container in the reagent list that corresponds to the respective reagent, and determine whether the mark in the mark button corresponding to each of the particularly selected reagent containers in the display list has been marked, and for each of the particularly selected reagent containers with the corresponding mark, change the respective mark buttons to a different color and change the respective marks to a different color for each of the particularly selected reagent containers with respective reagent remaining amounts less than or equal to the first predetermined threshold.

2. The automatic analyzer according to claim 1,
wherein the portable tablet terminal includes a barcode-reading camera capable of reading a barcode attached to each of the reagent containers set on the reagent container setting unit, and
wherein the portable tablet terminal determines the particularly selected reagent container selected by the operator based on barcode information attached to the particularly selected reagent container that is read by the barcode-reading camera, and updates the display of the reagent list by changing the displayed reagent list to identify the particularly selected reagent container selected by the operator.

3. The automatic analysis system according to claim 1, wherein the computer stores a third threshold for the reagent remaining amount for indicating a reminder level of the reminder information, and wherein the portable tablet terminal displays the reminder level on the reagent list based on the third threshold.

4. An automatic analyzer comprising:
a reagent container setting unit on which a plurality of reagent containers are set;
a reagent dispensing mechanism that aspirates a reagent from each of the reagent containers set on the reagent container setting unit;
a computer coupled to a wireless device; and
a portable tablet terminal wirelessly coupled to the computer,
wherein the computer is programmed to:
manage information related to the respective reagents of each of the reagent containers set on the reagent container setting unit, and
store reagent information related to a reagent remaining amount and a reagent expiration date of each of the reagent containers set on the reagent container setting unit,
wherein the portable tablet terminal includes a touch panel display unit,
wherein the portable tablet terminal is programmed to display a reagent list in which reminder information, which indicates a reminder to an operator, is assigned to each of a plurality of setting positions of particularly selected reagent containers among all of the reagent containers set on the reagent container setting unit based on the reagent information stored in the computer, the reagent list displaying information indicating the setting positions of each of the particularly selected reagent containers set on the reagent container setting unit, wherein the computer is programmed to update the display of the reagent list such that one or more of the particularly selected reagent container among all of the reagent containers selected by the operator is visually identifiable while the reagent list is displayed, wherein the portable tablet terminal is programmed to upon receiving the selection of the one or more of the particularly selected reagent containers via the touch panel display unit of the reagent list displayed on the display unit, determine the one or more of the particularly selected reagent containers selected by the operator and update the display of the reagent list to add or remove a mark indicating and corresponding to the one or more of the particularly selected reagent containers, wherein the reagent list includes a plurality of individual mark buttons respectively corresponding to each of the particularly selected reagent containers and are displayed separate from the information indicating the setting positions of the particularly selected reagent containers and are areas of the displayed reagent list that are designated for displaying an indication of whether a respective mark is displayed or not displayed for each of the particularly selected reagent containers, each mark indicating the corresponding mark button has been tapped via the touch panel display unit of the portable tablet terminal, wherein the computer is programmed to switch display of each respective mark button between displaying the mark and not displaying the mark within the respective mark button of the displayed reagent list, wherein the reagent list is a reagent disposal list wherein the particularly selected reagent containers indicate only a list of reagent containers in which a reagent remaining amount is zero and reagent containers in which the reagent expiration date is expired based on the information related to the reagent remaining amount and the reagent expiration date, wherein the reminder information is information indicating that the reagent remaining amount is zero or that the reagent expiration date is expired, wherein the computer is programmed to:

determine whether reagent remaining amounts of the reagents in the reagent containers are zero, and determine whether the mark in the mark button corresponding to each of the particularly selected reagent containers in the display list has been marked, and for each of the particularly selected reagent containers with the corresponding mark, change the respective mark buttons to a different color and change the respective marks to a different color for each of the particularly selected reagent containers with respective reagent remaining amounts equal to zero.

* * * * *